(12) United States Patent
Lee et al.

(10) Patent No.: US 10,350,254 B2
(45) Date of Patent: Jul. 16, 2019

(54) COMPOSITION FOR PREVENTING OR TREATING LIVER DISEASE, INCLUDING FRACTION OF MOUTAN CORTEX RADICIS EXTRACT

(71) Applicant: RESEARCH & BUSINESS FOUNDATION SUNGKYUNKWAN UNIVERSITY, Suwonsi, Gyeonggi-do (KR)

(72) Inventors: Sun-Mee Lee, Seoul (KR); Hong-Ik Cho, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/769,468

(22) PCT Filed: Oct. 17, 2016

(86) PCT No.: PCT/KR2016/011647
§ 371 (c)(1),
(2) Date: Apr. 19, 2018

(87) PCT Pub. No.: WO2017/069476
PCT Pub. Date: Apr. 27, 2017

(65) Prior Publication Data
US 2018/0303894 A1 Oct. 25, 2018

(30) Foreign Application Priority Data

Oct. 19, 2015 (KR) .................. 10-2015-0145335
Sep. 19, 2016 (KR) .................. 10-2016-0119284

(51) Int. Cl.
*A61K 36/65* (2006.01)
*A23L 33/105* (2016.01)
*A61P 1/16* (2006.01)

(52) U.S. Cl.
CPC ............ *A61K 36/65* (2013.01); *A23L 33/105* (2016.08); *A61P 1/16* (2018.01); *A23V 2002/00* (2013.01); *A23V 2200/30* (2013.01)

(58) Field of Classification Search
None
See application file for complete search history.

(56) References Cited

FOREIGN PATENT DOCUMENTS

| CN | 1899395 A | * | 1/2007 |
|----|-----------|---|--------|
| KR | 10-2007-0050998 A | | 5/2007 |
| KR | 10-2012-005617 A | | 1/2012 |
| KR | 10-2012-0061725 A | | 6/2012 |
| KR | 10-2015-0024608 A | | 3/2015 |

OTHER PUBLICATIONS

English translation of Lee (KR 10-2012-0005617)—dated Jan. 17, 2012.*
International Search Report for International Application No. PCT/KR2016/011647 (3 Pages) (dated Jan. 25, 2017).
Hu et al., "Paeonol, the main active principles of Paeonia mouton, ameliorates alcoholic steatohepatitis in mice", Journal of Ethnopharmacology, 2010, vol. 128, pp. 100-106.

* cited by examiner

*Primary Examiner* — Susan Hoffman
(74) *Attorney, Agent, or Firm* — NSIP Law

(57) ABSTRACT

The present invention relates to a composition containing a fraction of a Mouton Radicis Cortex extract, which can be advantageously used in the prevention or treatment of liver diseases. In the present invention, it was specifically verified that the use of the composition can effectively reduce the blood ALT concentration, inhibit the increase of TLR4 or IL-1β protein expression in the liver, and also inhibit the lipid peroxidation in the liver, and thus, it is expected that the composition can attain target therapy through a more fundamental approach in the prevention or treatment of liver diseases.

6 Claims, 11 Drawing Sheets

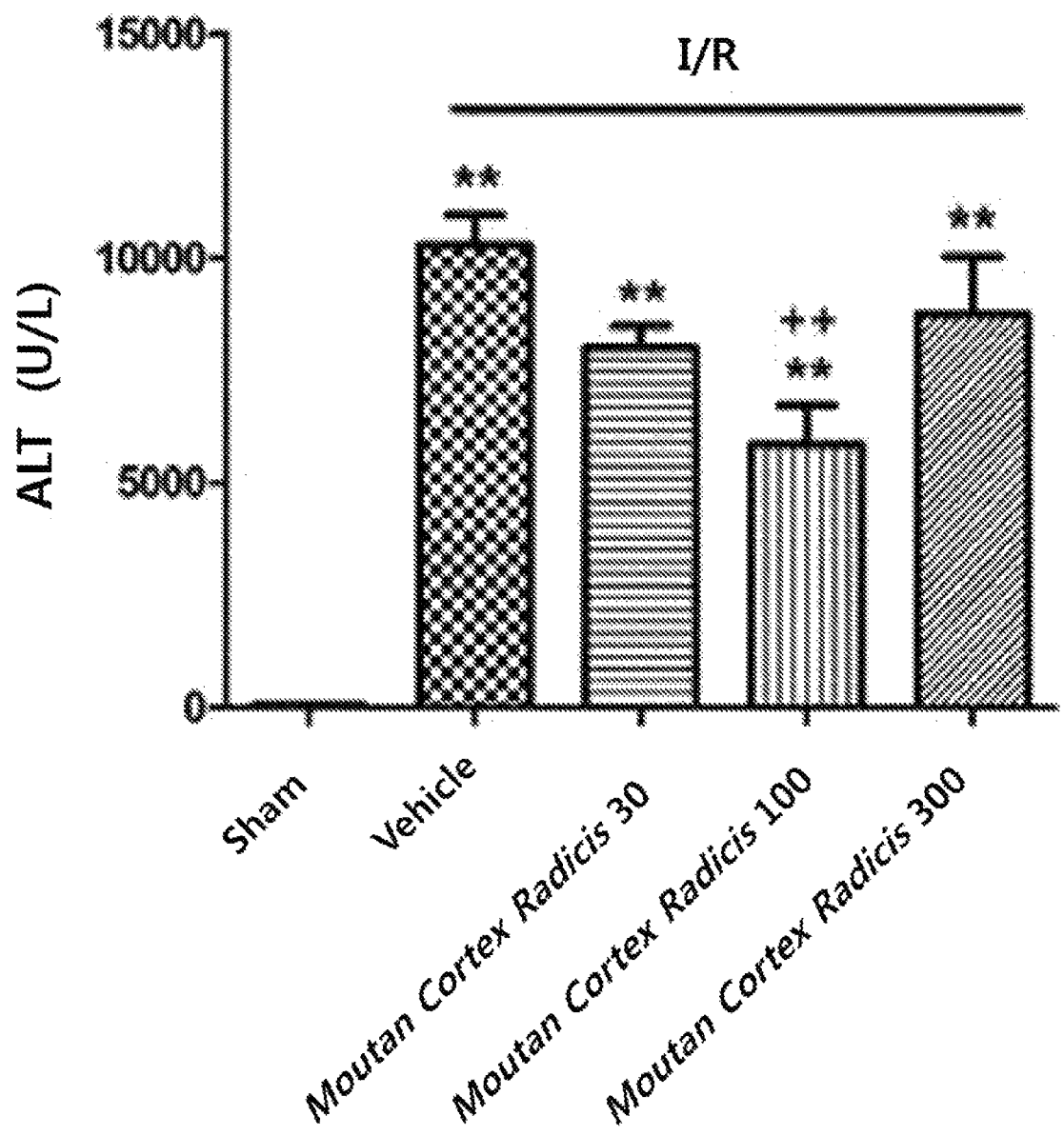
[Fig. 1]

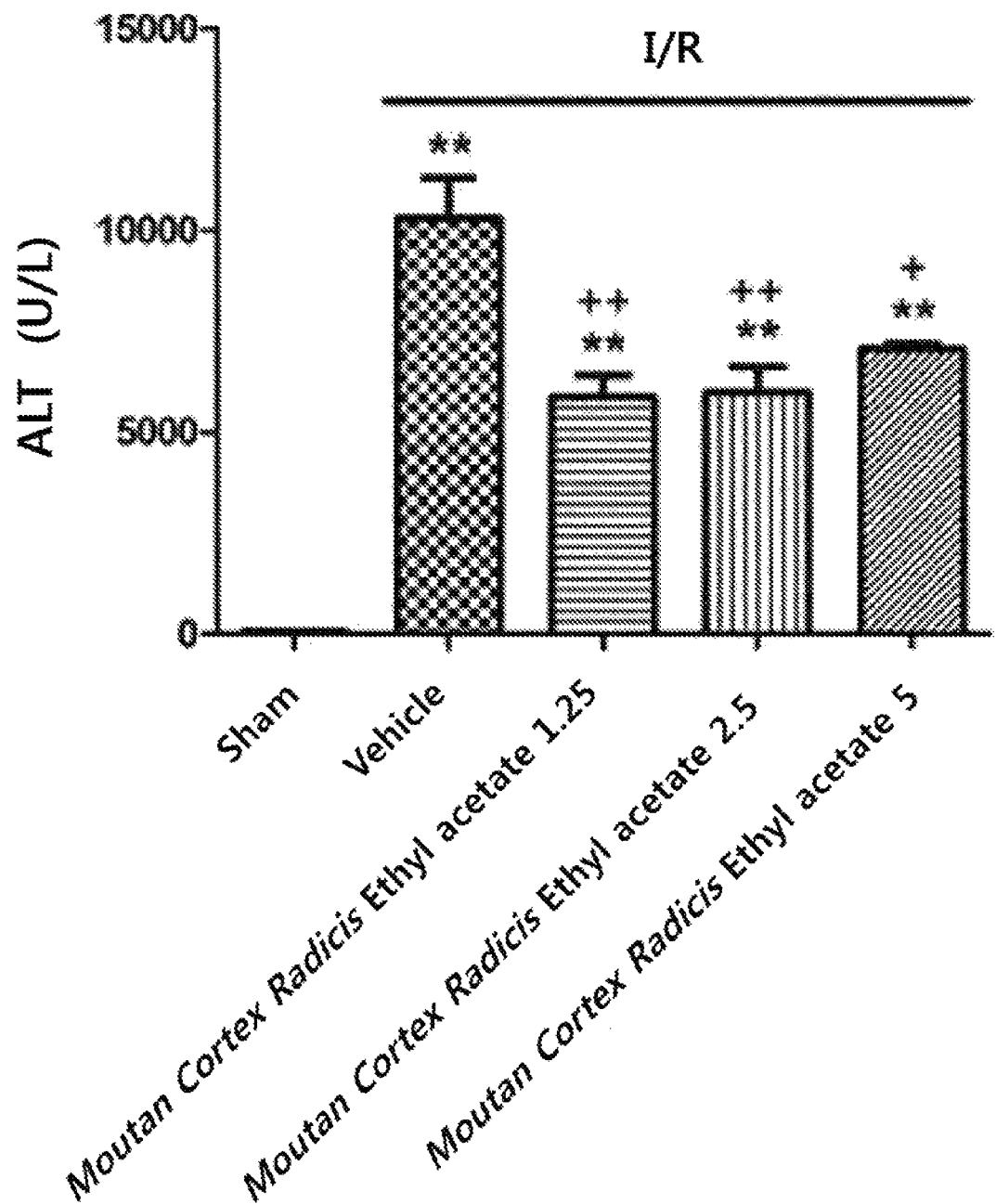
[Fig. 2a]

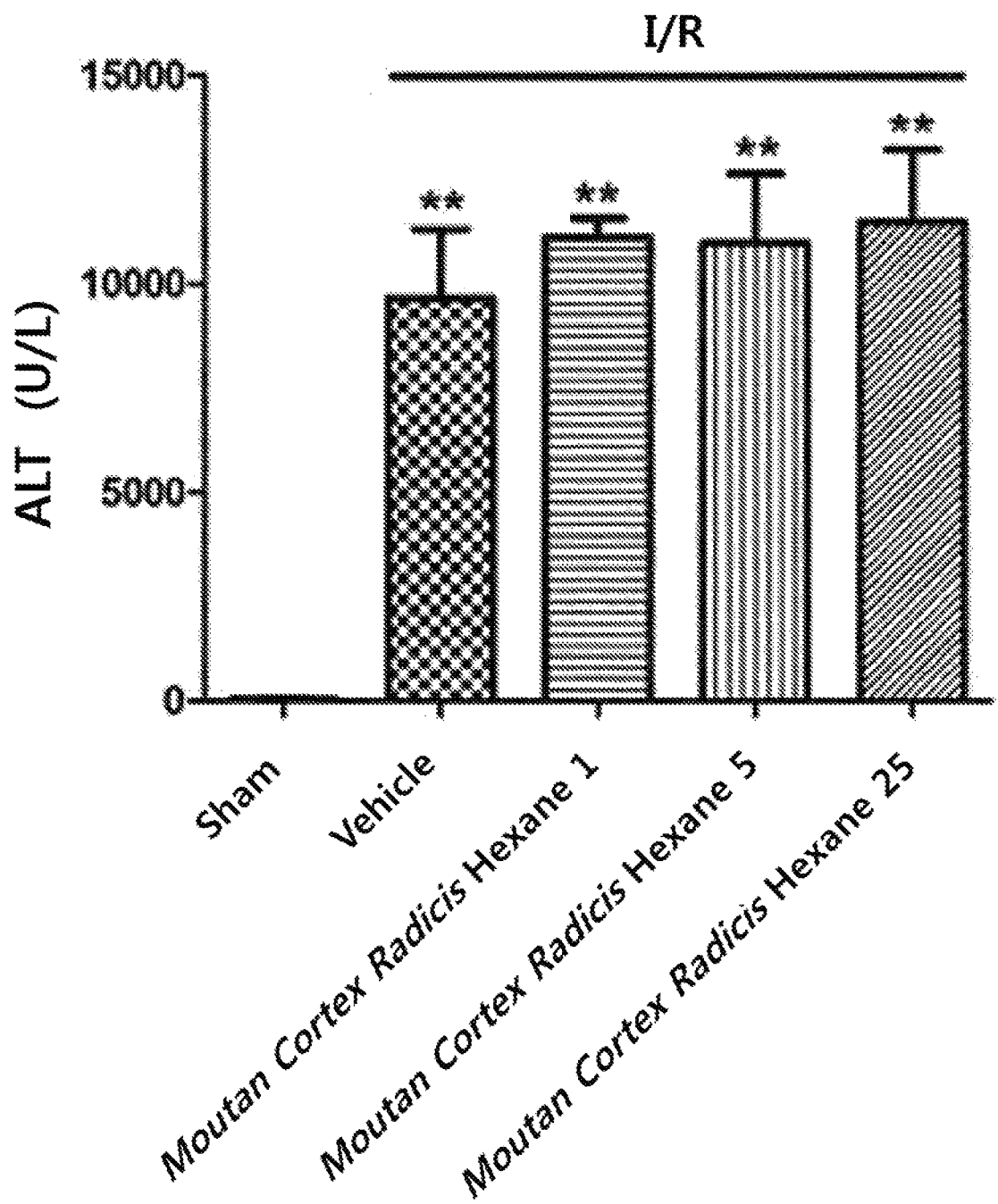
[Fig. 2b]

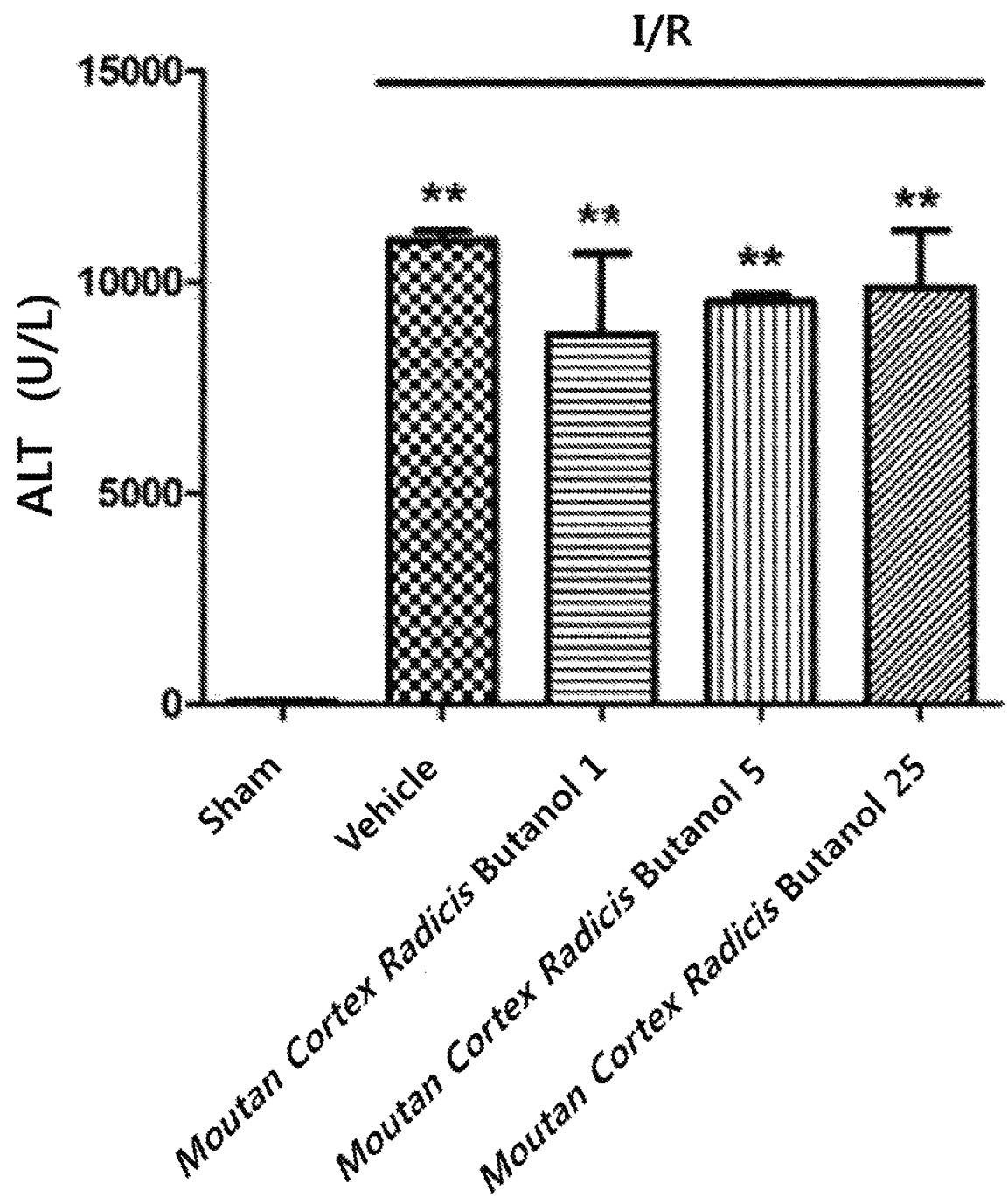
[Fig. 2c]

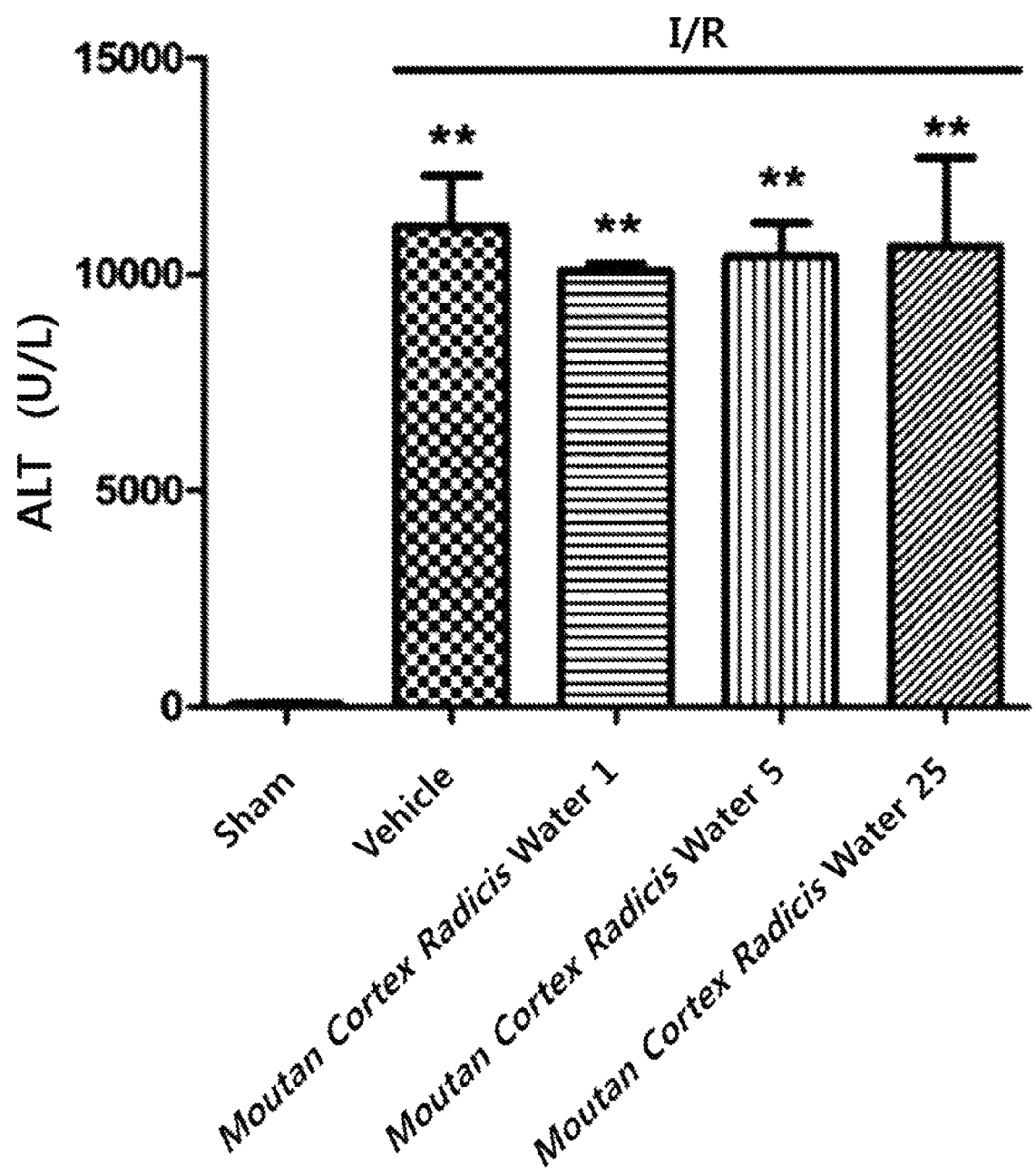
[Fig. 2d]

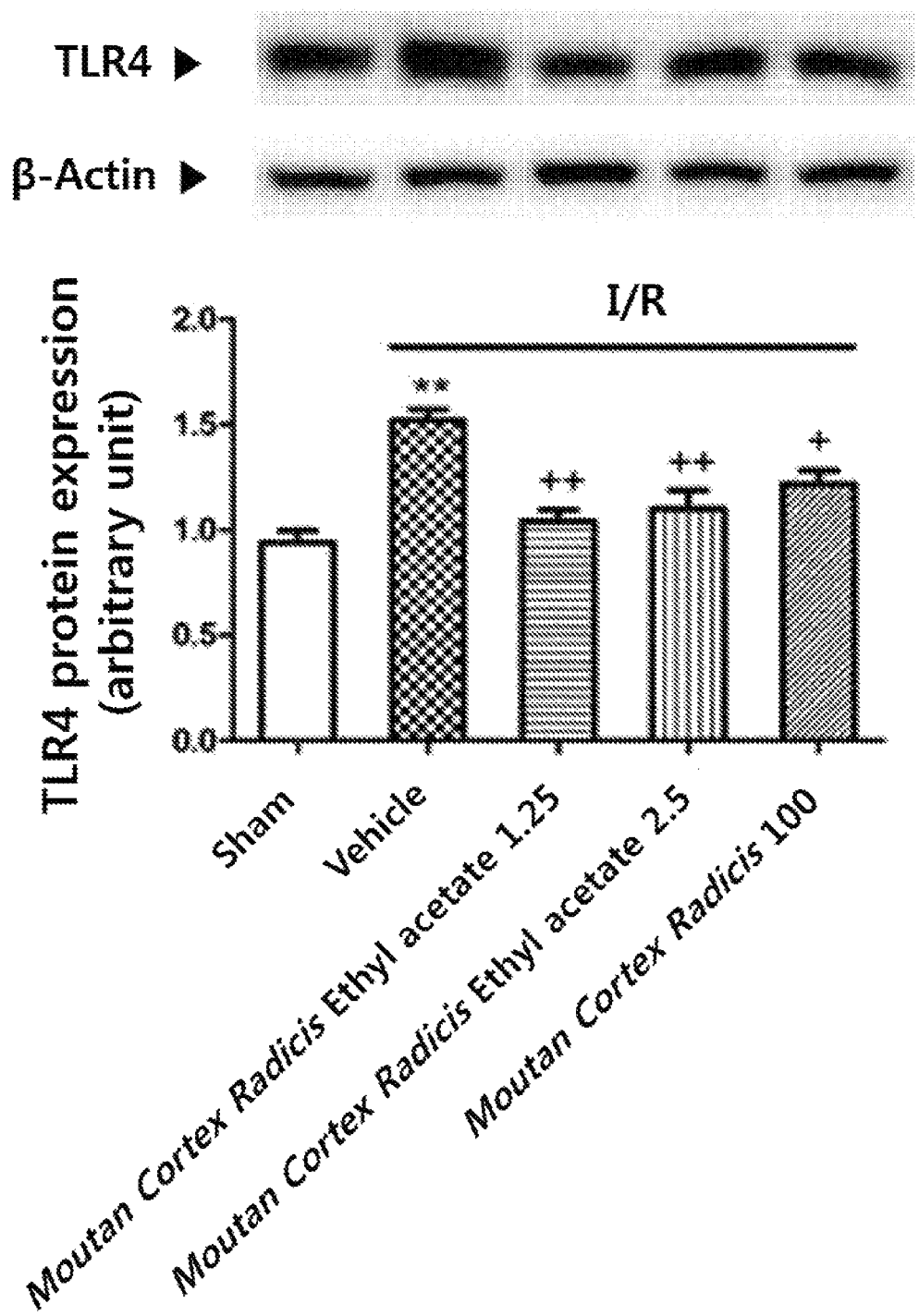
[Fig. 3a]

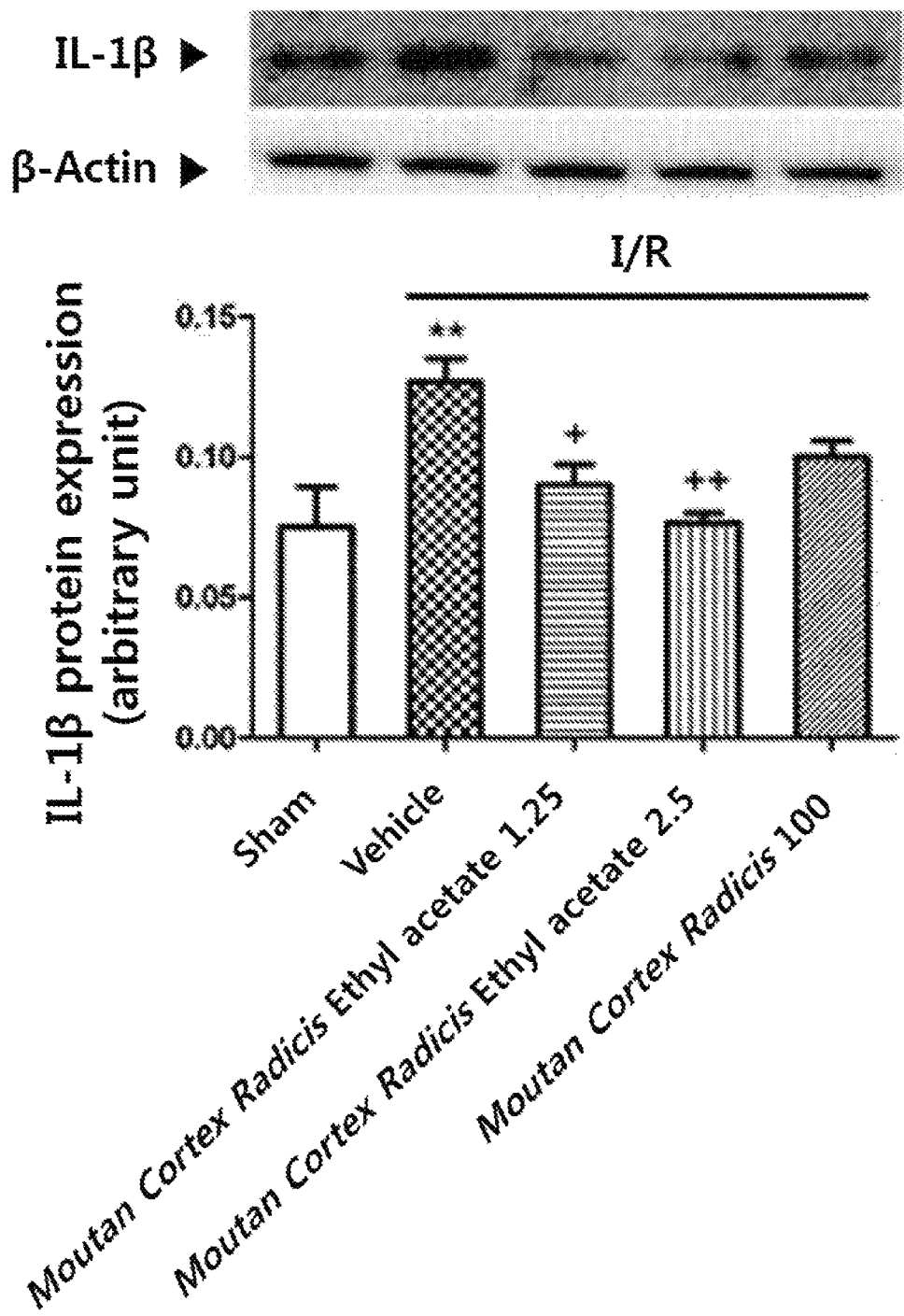
[Fig. 3b]

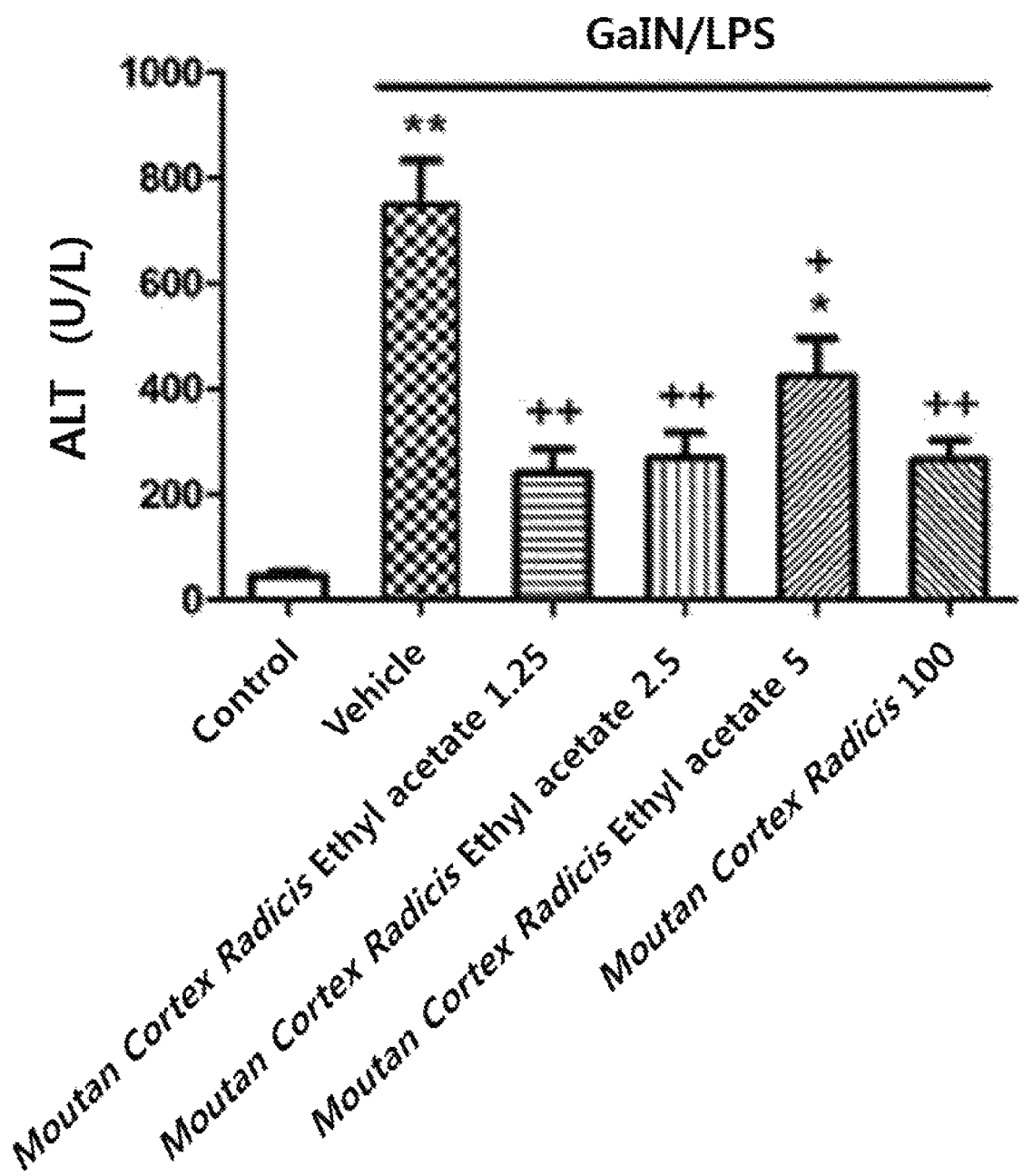
[Fig. 4]

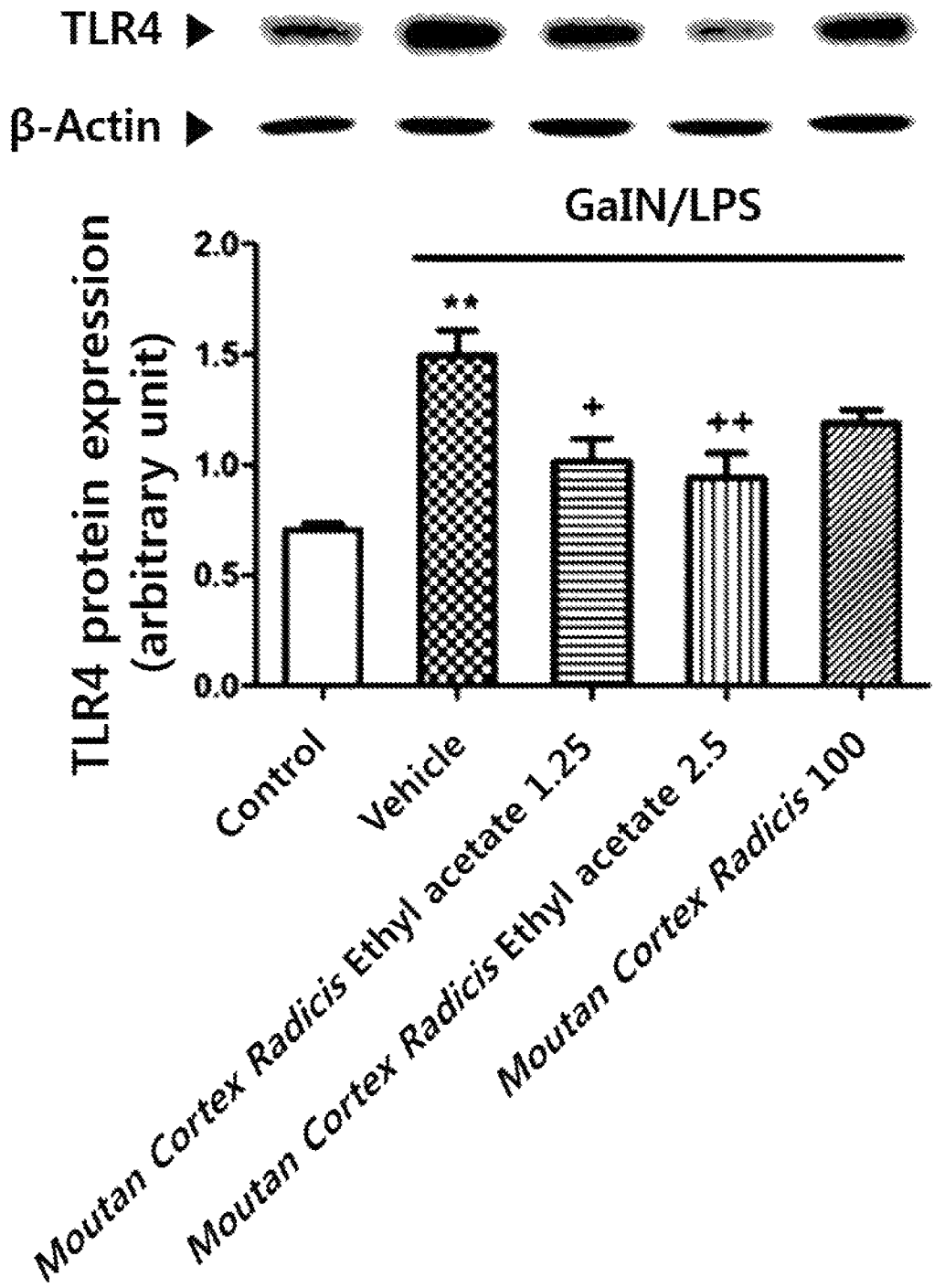
[Fig. 5]

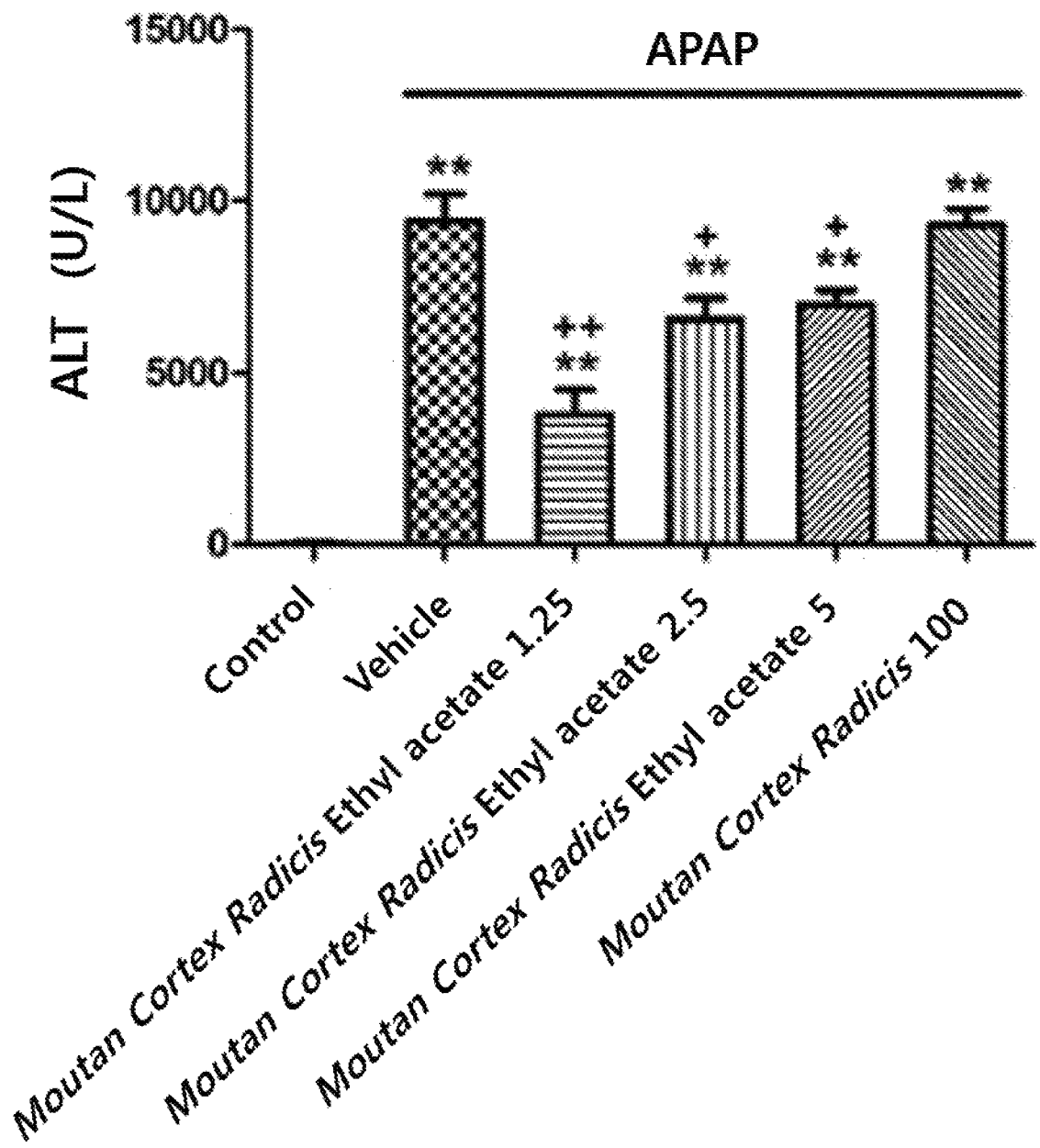
[Fig. 6]

[Fig. 7]
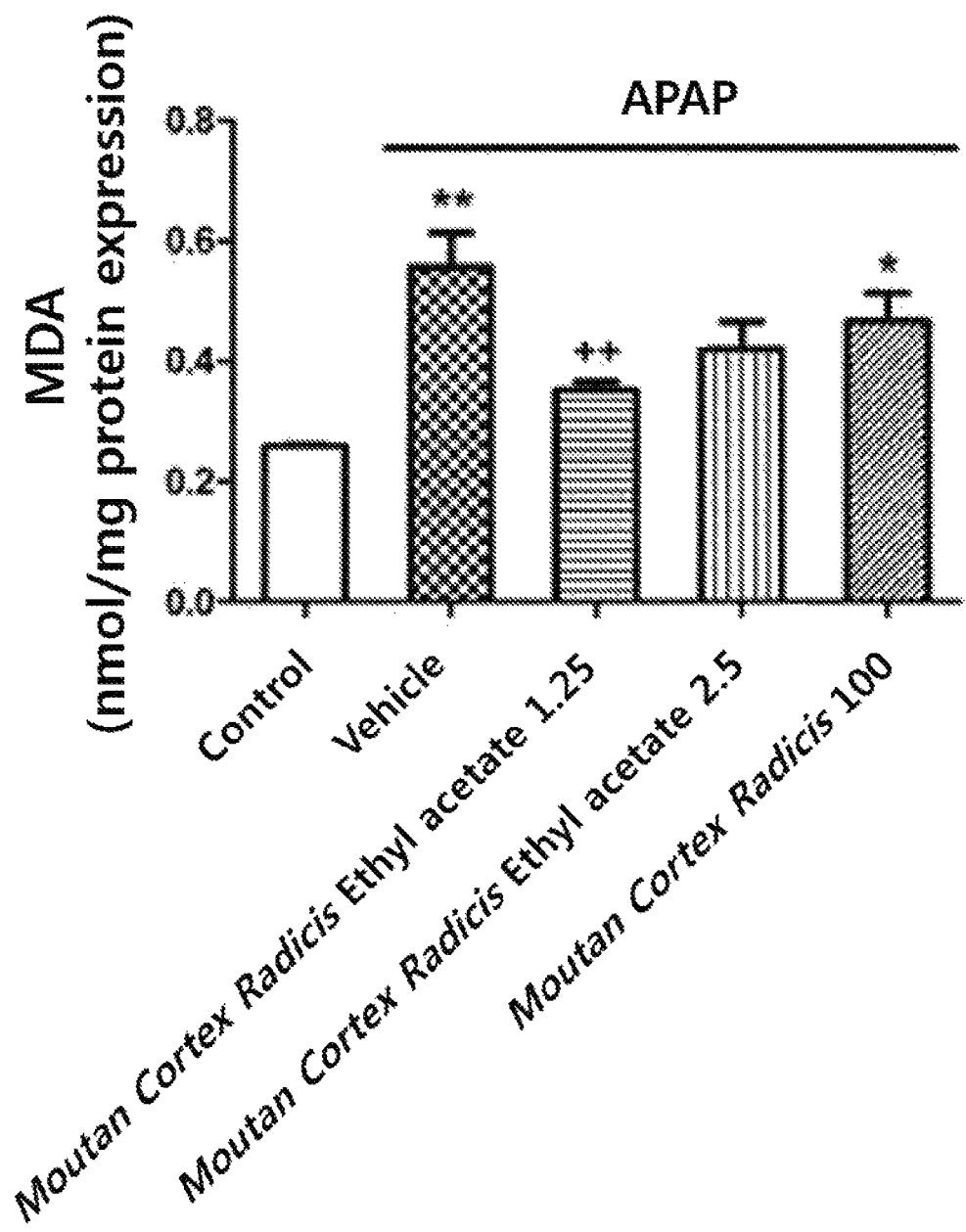

COMPOSITION FOR PREVENTING OR TREATING LIVER DISEASE, INCLUDING FRACTION OF MOUTAN CORTEX RADICIS EXTRACT

CROSS-REFERENCE TO RELATED APPLICATIONS

This application is a 371 of PCT/KR2016/011647, filed Oct. 17, 2016, which claims the benefit of priority from Korean Patent Application No. 10-2015-0145335, filed Oct. 19, 2015 and Korean Patent Application No. 10-2016-0119284, filed Sep. 19, 2016, the contents of each of which are incorporated herein by reference.

TECHNICAL FIELD

The present invention relates to a composition for preventing or treating a liver disease, which includes a fraction of a Moutan Cortex Radicis extract, and more particularly, to a pharmaceutical composition and health functional food composition for preventing or treating a liver disease, which include a fraction of a Moutan Cortex Radicis extract as an active ingredient.

BACKGROUND ART

The liver plays various roles in a body, such as lipid metabolism, detoxication, excretion of bile, storage of various nutrients, hematopoiesis or blood coagulation, and the control of a volume of circulating blood, and is one of the essential organs for supporting life. More specifically, first, the liver has a function of managing energy metabolism, so that all nutrients absorbed from food can be metabolized into substances capable of producing energy in the liver, and thus are provided to or stored in the entire body. Second, the liver has the function of synthesizing, storing and distributing approximately 2,000 enzymes, albumin, serum proteins of coagulation factors, bile acid, or lipids such as phospholipids and cholesterol. Third, as detoxication and degradation functions, the liver can detoxicate a drug, alcohol, or a toxic substance, excrete a variety of metabolites and have an immune function, which provides a critical role in life support.

Hepatitis, which represents inflammation in the liver, accounts for most of the liver diseases, and may be divided into acute hepatitis and chronic hepatitis according to modality, and may be divided into viral hepatitis, alcoholic hepatitis and drug-induced hepatitis according to cause. In addition, liver diseases caused by such abnormalities include fatty liver, hepatitis, liver cirrhosis and liver cancer. The pathogenesis of a liver disease has not been completely discovered, but it is known that fatty liver is primarily generated and then followed by secondary cell damage, and then a progressive liver disease such as steatohepatitis or liver cirrhosis is developed. In addition, since the liver disease is not found until it has progressed considerably due to no subjective symptom at an early stage, it is the leading cause of death not only in Korea but also in the world.

Currently, treatments for a liver disease, which have been generally used, are broadly divided into a dietary therapy and a drug therapy, and in most cases, these two methods are used together. The drug therapy against a liver disease may use drugs having various action mechanisms according to the cause and type of a liver disease, and examples of the drugs may generally be drugs, for example, hepatocyte regeneration promoters and liver-function supplements, such as ursodexoycholic acid, silymarine, biphenyldimethyldicarboxylate (DDB), glutathione, carnitine orotate, glycyrrhizin and multiple vitamins; antiviral agents such as acyclovir; immunosuppressants such as corticosteroid, 6-mercaptopurine (6-MP) and azathioprine; and fibrosis inhibitors such as D-penicillamine. However, due to limited hepatic protection and side effects of these agents, there is difficulty in using these drugs for fundamental treatment of a liver disease. Therefore, today, while there is a growing interest in natural substance-derived therapeutic agents for a liver disease, which have excellent biocompatibility with little concern about side effects, and such therapeutic agents become the subject of a major project (Korean Patent Application Publication No. 10-2015-0098161). However, in the case of most natural substances, little basic research on an effective dose and an exact pharmacological effect was investigated, and thus the use thereof as a therapeutic agent for a liver disease is difficult.

Meanwhile, Moutan Cortex Radicis, the root bark of *Paeonia suffruticosa* Andrews (Paeoniaceae), has been widely used to eliminate heat from the blood and blood stasis by promoting active blood circulation, and treat ischemia in oriental medicine. A Moutan Cortex Radicis extract has been reported to inhibit the release of IL-8 and MCP-1, which are chemokines, in vitro, and the expression of iNOS and COX-2, which are inflammatory mediators. The Moutan Cortex Radicis extract has been known to have a very high inhibitory activity against HIV integrase, and it has been known that paeonol, a main component of Moutan Cortex Radicis, inhibits xanthine oxidase to inhibit the generation of reactive oxygen species, and inhibits the release of an inflammatory mediator, TNF-α.

Against this backdrop, the inventors made an effort to find a natural substance as an agent for preventing or treating a liver disease, and when a fraction of the Moutan Cortex Radicis extract was treated to cure various types of liver injury including impaired blood flow caused by hepatic ischemia and reperfusion, acute hepatic failure caused by galactosamine/lipopolysaccharide (GalN/LPS) and drug-mediated liver injury caused by acetaminophen (APAP), the fraction has an excellent liver protective effect, and therefore the present invention was completed.

DISCLOSURE

Technical Problem

The present invention is provided to solve the above-described problems, and the inventors confirmed a reduction effect on a blood ALT concentration due to the treatment of a fraction of a Mouton Cortex Radicis extract, an inhibitory effect on TLR4 protein expression in the liver, an inhibitory effect on IL-1β protein expression in the liver, and an inhibitory effect on lipid peroxidation in the liver, and based on this, the present invention was completed.

Therefore, the present invention is directed to providing a composition for preventing or treating a liver disease, which includes an ethyl acetate fraction of a Mouton Cortex Radicis extract as an active ingredient.

The present invention is also directed to providing a health functional food composition for preventing or improving a liver disease, which includes an ethyl acetate fraction of a Mouton Cortex Radicis extract as an active ingredient.

However, technical problems to be solved in the present invention are not limited to the above-described problems, and other problems which are not described herein will be fully understood by those of ordinary skill in the art from the following descriptions.

Technical Solution

To achieve the objects of the present invention described above, the present invention provides a pharmaceutical composition for preventing or treating a liver disease, which includes a fraction of a Mouton Cortex Radicis extract as an active ingredient.

In an exemplary embodiment of the present invention, the extract may be obtained through extraction with one or more solvents selected from the group consisting of water, alcohols having 1 to 4 carbon atoms, and a mixture thereof.

In another exemplary embodiment of the present invention, the fraction may be obtained by fractionating the Moutan Cortex Radicis extract with one or more solvents selected from the group consisting of hexane, butanol, methylene chloride, acetone, ethyl acetate, ethyl ether, chloroform, water, and a mixture thereof, and the solvent is preferably water, hexane, butanol, or ethyl acetate, and more preferably, ethyl acetate.

In still another exemplary embodiment of the present invention, the liver disease may be selected from the group consisting of hepatitis, hepatotoxicity, cholestasis, fatty liver, liver cirrhosis, liver ischemia, an alcoholic liver disease, a liver abscess, hepatic coma, liver atrophy, and liver cancer.

In yet another exemplary embodiment of the present invention, the composition may inhibit an increase in blood alanine aminotransferase (ALT) concentration.

In yet another exemplary embodiment of the present invention, the composition may inhibit an increase in the expression level of toll-like receptor (TLR) 4 or interleukin 1 beta (IL-1β) protein in the liver.

In yet another exemplary embodiment of the present invention, the composition may inhibit lipid peroxidation in the liver.

The present invention provides a health functional food composition for preventing or improving a liver disease, which includes a fraction of a Moutan Cortex Radicis extract as an active ingredient.

The present invention provides a method for preventing or treating a liver disease, which includes administering the pharmaceutical composition into a subject.

The present invention provides a novel use of a fraction of a Moutan Cortex Radicis extract for preparing an agent for treating a liver disease.

Advantageous Effects

A composition according to the present invention includes a fraction of a Mouton Cortex Radicis extract as an active ingredient, and can effectively reduce a blood ALT concentration, which is an indicator of liver injury, inhibit an increase in TLR4 or IL-1β protein expression in the liver and inhibit lipid peroxidation in the liver by using the composition. Therefore, as the composition of the present invention uses a natural substance-derived active ingredient, it has excellent liver protection efficacy, and almost no toxicity and side effects, and thus can be used in a body for a long period of time. Therefore, the composition is expected to be useful in prevention or treatment of a liver disease.

DESCRIPTION OF DRAWINGS

FIG. 1 shows a result of comparing changes in ALT activity according to the treatment of a Moutan Cortex Radicis extract (30, 100 and 300 mg/kg), with respect to impaired blood flow caused by hepatic ischemia and reperfusion.

FIG. 2A shows a result of comparing changes in ALT activity according to the treatment of an ethyl acetate fraction of a Moutan Cortex Radicis extract (1.25, 2.5 and 5 mg/kg), FIG. 2B shows a result of comparing changes in ALT activity according to the treatment of a hexane fraction of the Moutan Cortex Radicis extract (1, 5 and 25 mg/kg), FIG. 2C shows a result of comparing changes in ALT activity according to the treatment of a butanol fraction of the Moutan Cortex Radicis extract (1, 5 and 25 mg/kg), and FIG. 2D shows a result of comparing changes in ALT activity according to the treatment of a water fraction of the Moutan Cortex Radicis extract (1, 5 and 25 mg/kg), with respect to impaired blood flow caused by hepatic ischemia and reperfusion.

FIG. 3A shows a result of comparing TLR4 protein expression levels according to the treatment of an ethyl acetate fraction of a Moutan Cortex Radicis extract (1.25 and 2.5 mg/kg), and FIG. 3B shows a result of comparing IL-1β protein expression levels according to the treatment of the ethyl acetate fraction of the Moutan Cortex Radicis extract (1.25 and 2.5 mg/kg), with respect to impaired blood flow caused by hepatic ischemia and reperfusion.

FIG. 4 shows a result of comparing changes in ALT activity according to the treatment of an ethyl acetate fraction of a Moutan Cortex Radicis extract (1.25, 2.5 and 5 mg/kg), with respect to acute hepatic failure caused by GalN/LPS.

FIG. 5 shows a result of comparing a change in TLR4 or IL-1β protein expression level according to the treatment of an ethyl acetate fraction of a Moutan Cortex Radicis extract (1.25, 2.5 and 5 mg/kg), with respect to acute hepatic failure caused by GalN/LPS.

FIG. 6 shows a result of comparing changes in ALT activity according to the treatment of an ethyl acetate fraction of a Moutan Cortex Radicis extract (1.25, 2.5 and 5 mg/kg), with respect to APAP-induced liver injury.

FIG. 7 shows a result of comparing changes in malondialdehyde (MDA) levels according to the treatment of an ethyl acetate fraction of a Moutan Cortex Radicis extract (1.25, 2.5 and 5 mg/kg), with respect to APAP-induced liver injury.

MODES OF THE INVENTION

The present invention includes a composition for preventing or treating a liver disease, which includes a fraction of a Moutan Cortex Radicis extract as an active ingredient, and the composition includes a pharmaceutical composition or a health functional food composition.

Particularly, since the present invention is extracted from a natural substance, despite long-term administration, it has less side effects than a conventional therapeutic agent has and exhibits an inhibitory effect on hepatocellular necrosis and liver injury. Therefore, it can be effectively used to prevent or treat a liver disease.

The term "Moutan Cortex Radicis" used herein refers to a herbal medicine made of the root bark of *Paeonia suffruticosa* Andrews (Paeoniaceae), used for treatment of a menstrual irregularity caused by blood heat, menstrual cramps, bruises, hematemesis, epistaxes, spots, and bone twinges caused by a consumptive fever, the elevation of blood pressure, the elimination of blood stasis, contusions, an anti-inflammatory purpose and pain relief, the treatment of an abscess, or the treatment of early-stage appendicitis.

As the major pharmacological actions of Moutan Cortex Radicis, analgesic, sedative, antipyretic, anticonvulsant, antiinflammatory, antithrombotic and antiallergic actions, and inhibitory actions against gastric secretions and uterine mucosal hemorrhages, and an antibacterial action have been reported.

In the present invention, a Moutan Cortex Radicis extract is prepared from Moutan Cortex Radicis using an extraction solvent and then fractionated, thereby preparing a fraction of a Moutan Cortex Radicis extract of the present invention.

Here, the Moutan Cortex Radicis extract may be obtained using a conventional solvent according to a well-known conventional method for extracting an extract from a natural substance, that is, under generally-used temperature and pressure conditions using a conventional solvent. For example, in the present invention, the Moutan Cortex Radicis extract may be extracted using one or more solvents selected from the group consisting of water, alcohols having 1 to 4 carbon atoms and a mixture thereof, and preferably ethanol. The Moutan Cortex Radicis extract may be extracted by various methods such as hot-water extraction, cold-water extraction, heat reflux extraction, ultrasonic extraction, but the present invention is not limited thereto.

Afterward, to remove a solvent, the prepared extract may be filtered, concentrated or dried, or all of filtering, concentrating and drying may be performed. For example, filtration may be performed using filter paper or a vacuum filter, concentration may be performed using a vacuum concentrator, drying may be performed by lyophilization, but the present invention is not limited thereto.

In addition, the extract extracted with the solvent undergoes fractionation with a solvent selected from the group consisting of hexane, butanol, methylene chloride, acetone, ethyl acetate, ethyl ether, chloroform, water and a mixture thereof. The extract is preferably water, hexane, butanol and ethyl acetate, and more preferably ethyl acetate, but the present invention is not limited thereto.

Meanwhile, the "liver disease", which is a disease needed to be improved, prevented or treated by the composition of the present invention, means that there is a problem with one or more of the various functions that are performed by the liver, and thus metabolism may not be normally performed. The most frequent type of liver disease is hepatitis, which is divided into acute hepatitis and chronic hepatitis. Generally, the acute hepatitis is easily cured and benign. The acute hepatitis includes viral hepatitis, alcoholic hepatitis, and addictive hepatitis by cause, and currently, the most common liver disease is viral hepatitis. The liver disease may be, but is not limited to, hepatitis, hepatotoxicity, cholestasis, fatty liver, liver cirrhosis, liver ischemia, an alcoholic liver disease, a liver abscess, hepatic coma, liver atrophy and liver cancer.

The fraction of a Moutan Cortex Radicis extract of the present invention may inhibit the increase in blood ALT concentration in hepatocytes.

The term "alanine aminotransferase (ALT)" used herein refers to an enzyme which is present in a large amount in hepatocytes and a specific indicator of a liver disease. The normal range of ALT is 7 to 56 units per liter of serum. The enzyme catalyzes an intercellular chemical reaction transferring an amino group from a donor molecule to a recipient molecule, and since it is present in a large amount in hepatocytes, is used as a specific indicator representing a liver condition.

The fraction of a Moutan Cortex Radicis extract of the present invention may inhibit an increase in the protein expression level of TLR 4 in liver tissue.

The term "TLR 4 protein" used herein refers to one of the receptors directly recognizing a unique molecular pattern of a component constituting a pathogen in a natural aspect of early-stage biodefense against pathogens such as bacteria, viruses, parasites, etc., and is used as an indicator recognizing a gram-negative bacteria-derived lipid polysaccharide (LPS).

The fraction of a Moutan Cortex Radicis extract of the present invention may inhibit an increase in IL-1$\beta$ protein expression level in liver tissue.

The term "interleukin 1 beta (IL-1$\beta$) protein" used herein refers to one of the interleukin-1 family, which are monokines produced by monocytes and macrophages, and corresponds to an inflammatory cytokine. The IL-1$\beta$ protein is used as an indicator recognizing inflammation in the liver.

The fraction of a Moutan Cortex Radicis extract of the present invention may inhibit lipid peroxidation in liver tissue.

The term "lipid peroxidation" used herein refers that a lipid is peroxidized by adding oxygen to a lipid component such as an unsaturated fatty acid. Since a peroxidized lipid produced in a living body damages a biomembrane system, and dysfunction or necrosis of cells is caused by modifying enzymes, hormones, vitamins, etc., it can be used as a clinical indicator of a liver disease.

However, the term "prevention" used herein refers to all actions of inhibiting a liver disease or delaying the onset thereof by administration of the pharmaceutical composition according to the present invention.

In addition, the term "treatment" used herein refers to all actions involved in alleviating or beneficially changing symptoms of a liver disease by administration of the pharmaceutical composition according to the present invention.

In an exemplary embodiment of the present invention, in animal models with various types of liver injury including impaired blood flow caused by hepatic ischemia and reperfusion, acute hepatic failure caused by galactosamine/lipopolysaccharide (GalN/LPS) and APAP-induced liver injury, the Moutan Cortex Radicis extract or a fraction of the extract is treated to confirm a therapeutic effect on liver injury. As a result, in a group treated with a fraction of the Moutan Cortex Radicis extract, a blood ALT concentration, which is an indicator representing liver injury, was significantly reduced. This result is significantly superior to that of a group treated with the Moutan Cortex Radicis extract, and particularly, in the case of a fraction using an ethyl acetate solvent, compared with other solvent groups, more superior effects were exhibited. Therefore, it was confirmed that the Moutan Cortex Radicis extract can be very effectively used as a pharmaceutical composition for preventing or treating a liver disease (refer to Examples 2 to 5).

The pharmaceutical composition according to the present invention may include a pharmaceutically acceptable carrier, in addition to the active ingredient. Here, the pharmaceutically acceptable carrier is generally used in formulation, and includes lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, but the present invention is not limited thereto. In addition, the pharmaceutical composition according to the present invention may further include a lubricant, a wetting agent, a sweetening agent, a flavoring agent, an emulsifier, a suspending agent or a preservative, in addition to the above-mentioned components.

The pharmaceutical composition of the present invention may be administered orally or parenterally (e.g., intravenously, subcutaneously, intraperitoneally or locally) depending on a desired method, and a dose of the pharmaceutical composition may vary depending on the condition and body weight of a patient, the severity of a disease, a drug type, an administration route and time, and may be suitably selected by one of ordinary skill in the art.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, and may be administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the pharmaceutical composition of the present invention may be dependent on a patient's age, sex, condition and body weight, an absorption rate of the active ingredient in the body, an inactivation rate, an excretion rate, a type of disease, or a drug used in combination, and may be generally administered at 100 to 500 mg/kg of body weight daily or every other day, or divided into one or three daily administrations. However, the effective amount may vary depending on an administration route, the severity of obesity, sex, body weight or age, and therefore, the scope of the present invention is not limited by the dose in any way.

In addition, the present invention provides a health functional food composition for preventing or improving a liver disease, which includes a fraction of a Moutan Cortex Radicis extract as an active ingredient.

The term "improvement" used herein refers to all types of actions that at least reduce parameters related to a condition to be treated, for example, a degree of a symptom. Here, to prevent or ameliorate a liver disease, the health functional food composition may be used simultaneously or separately with a therapeutic agent before or after the onset of the corresponding disease.

In the functional food composition of the present invention, the active ingredient may be added as is to food or used in combination with other food or food ingredients, and the functional food composition may be suitably used according to a conventional method. A mixing amount of the active ingredient may be suitably determined according to a purpose of its use (prevention or amelioration). Generally, in preparation of food or drinks, the composition of the present invention is added at 15 wt % or less, and preferably, 10 wt % or less with respect to the raw material. However, in the case of long-term intake for healthcare and sanitation, or health control, the amount may be less than the above range.

The health functional food composition of the present invention has no specific limit on other ingredients, except containing of the active ingredient described above at a predetermined ratio, and may contain various flavoring agents or natural carbohydrates as additional ingredients like general beverages. Examples of the above-mentioned natural carbohydrates include common saccharides including monosaccharides such as glucose, fructose, etc., disaccharides such as maltose, sucrose, etc., and polysaccharides such as dextrin, cyclodextrin, etc.; and sugar alcohols such as xylitol, sorbitol, erythritol, etc. Other than the above-described flavoring agents, natural flavoring agents (thaumatin, *stevia* extracts (e.g., rebaudioside A, glycyrrhizin, etc.)) and synthetic flavoring agents (saccharin, aspartame, etc.) may be preferably used as a flavoring agent. The relative amount of the natural carbohydrate may be suitably determined by the choice of one of ordinary skill in the art.

In addition to the above-mentioned ingredients, the health functional food composition of the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, a protective colloid thickening agent, a pH regulator, a stabilizer, a preservative, glycerin, alcohol, or a carbonating agent used for soft drinks. Such ingredients may be used alone or in combination. The relative amounts of such additives may also be suitably selected by one of ordinary skill in the art.

In a different aspect of the present invention, the present invention provides a method for treating a liver disease, which includes administering the pharmaceutical composition into a subject. The term "subject" used herein refers to a subject in need of treatment, and more specifically, a mammal such as a human, or a non-human primate, a mouse, a rat, a dog, a cat, a horse, and a cow.

Hereinafter, to help in understanding the present invention, exemplary examples will be suggested. However, the following examples are merely provided to more easily understand the present invention, and not to limit the present invention.

EXAMPLES

Example 1. Experimental Preparation and Method 1-1 Extraction of Moutan Cortex Radicis Extract and Fraction Thereof 300 g of standardized Moutan Cortex Radicis (Herbal Medicine Pharmacist) was prepared. The Moutan Cortex Radicis was extracted twice using 70% ethanol as an extraction solvent by performing digestion (at 55 to 60° C.) under reflux for 5 hours. The filtrate obtained by the extraction was vacuum-concentrated to remove the 70% ethanol, thereby obtaining a Moutan Cortex Radicis extract. A yield of the final Moutan Cortex Radicis extract was 55.8 g, and a percent yield thereof was 18.6%. Afterward, 40 g of the 70% ethanol extract was suspended in 400 ml of distilled water, and sequentially distributed and extracted three times using each of the same amount of hexane, ethyl acetate (EA), butanol and water as solvents. All the obtained solvent fractions were concentrated under reduced pressure, thereby obtaining hexane, ethyl acetate, butanol and water fractions at 2.1, 5.3, 4.2 and 17.6 g, respectively.

1-2. Experimental Animals

For experimental animals, ICR-strain male mice (21 to 23 g) were provided from Daehan BioLink Co. Ltd., and acclimated for one week before being used in the experiments. All experimental animals were acclimated in a laboratory which had a regulated temperature and a 12-hour dark cycle, and solid feed (Daehan BioLink Co. Ltd.) and water were freely fed. All of the animal experiments were approved by the Animal Experiment Ethics Committee of the School of Pharmacy at Sungkyunkwan University, and carried out according to the guidelines of the National Institutes of Health (NIH publication No. 86-23, revised 1985).

1-3. Hepatic Ischemia and Reperfusion Injury

Mice were fasted for 18 hours, anesthetized with ketamine (6 mg/kg) and xylazine (8 mg/kg), and cut along the midline at the abdomen. Ischemia was induced for 60 minutes by clamping the hepatic artery and biliary tract, which play a major role in oxygen supply into the left branch of a portal vein and the liver, and then the clamps were removed to cause reperfusion. Five hours after the reperfusion, blood was collected from the abdominal aorta, the left lobe and the median lobe of the liver were extracted and stored at −80° C. until analysis. A control group (sham) underwent the same process as described above, except that the left branch of the portal vein, the hepatic artery and the biliary tract were not clamped.

The Moutan Cortex Radicis extract or a fraction thereof was orally administered once a day for 2 days at the same point of time from two days before surgery (48 hours and 24 hours before hepatic ischemia surgery), and orally administered one hour before the surgery on the day of the surgery.

1-4. GalN/LPS-Induced Acute Liver Failure

Mice were fasted for 18 hours, and intraperitoneally administered GalN (800 mg/kg) and LPS (40 µg/kg). Six hours after the GalN/LPS administration, blood was collected from the abdominal aorta, and the left lobe and median lobe of the liver were extracted and stored at 80° C. until analysis. A control group (sham) underwent the same process as described above, except that mice were intraperitoneally administered only normal saline.

The experimental substance was orally administered once a day for 2 days at the same point of time from two days before the GalN/LPS administration (48 hours and 24 hours before the GalN/LPS administration), and orally administered one hour before the GalN/LPS administration on the day of the GalN/LPS administration.

1-5. APAP-Induced Liver Injury

The mice were fasted for 18 hours, and intraperitoneally administered APAP (400 mg/kg). Twenty-four hours after the APAP administration, blood was collected from the abdominal aorta, and the left lobe and median lobe of the liver were extracted and stored at −80° C. until analysis. A control group (sham) underwent the same process as described above, except that mice were intraperitoneally administered only with normal saline.

The experimental substance was orally administered once a day for 2 days at the same point of time from two days before the APAP administration (48 hours and 24 hours before the APAP administration), and orally administered one hour before the APAP administration on the day of the APAP administration.

1-6. Confirmation of Blood ALT Activity

Blood ALT activity was measured with a spectrophotometer (UV-1601, Simadzu, Japan) using an IVD Lab kit (IVD Lab, Korea).

1-7. Confirmation of TLR4 and IL-1β Protein Expression Levels in Liver Tissue

Proteins were extracted by homogenizing liver tissue in a RIPA protein extraction solution (CellNest, Korea) in a 10-fold volume, centrifuged at 13,000×g and 4° C. for 6 minutes to obtain only a supernatant. The obtained supernatant was quantified using a BCA protein assay kit (Pierce Biotechnology, IL, USA), mixed with a 2× Western sample buffer at 1:1, heated in boiling water for 7 minutes for denaturation. The protein sample (16 µg) was separated through SDS-PAGE, and then transferred onto a polyvinylidene fluoride membrane (Millipore, MA, USA) through electrophoresis using the Semi-Dry Trans-Blot Cell (Bio-Rad Laboratories, CA, USA). The resulting membrane was washed with TBS/T, and then blocked with 5% (w/v) skim milk-added TBS/T for 1 hour at room temperature. The membrane was reacted with primary antibodies at 4° C. for 12 hours and secondary antibodies at room temperature for 1 hour, and colorized using an ECL detection system (iN-tRON Biotechnology Inc.).

Each band was quantified using TOTALLAB TL 120 software (Nonlinear Dynamics Ltd., Newcastle, GB). The used primary antibodies are as follows: TLR4 (1:10000 dilution, Santa Cruz Biotechnology Inc., CA, USA), IL-1β (1:2500 dilution, BioVision, CA, USA) and β-actin (1:5000 dilution, Sigma Aldrich, MO, USA). Evaluation results are normalized with β-actin.

1-8. Confirmation of Lipid Peroxidation in Liver Tissue

To measure an amount of malondialdehyde (MDA), which is the final product of lipid peroxidation, the homogenized liver tissue suspension was treated with thiobarbituric acid to allow a reaction, and spectrophotometrically analyzed at 535 nm using 1,1,3-3 tetraethoxy propane (Sigma Aldrich) as a standard substance.

1-9. Statistical Analysis

All experimental results were expressed as mean±standard errors, and the statistical analysis for these results was conducted through one-way ANOVA to determine statistical significance at the $P<0.05$ level.

Example 2. Confirmation of Effect of Moutan Cortex Radicis Extracton Blood ALT Activity in the Case of Hepatic Ischemia and Reperfusion Injury In this example, to confirm a liver protective effect according to the treatment of the Moutan Cortex Radicis extract by comparing blood ALT activity, which is an indicator of hepatocytic injury, an experiment was carried out according to the methods described in Examples 1-3 and 1-6.

Consequently, as shown in FIG. 1, while the blood ALT activity of a mouse (sham) before hepatic ischemia surgery was 63.1±7.4 U/L, 5 hours after reperfusion, the blood ALT activity of a control group (vesicle) has increased 163.1-fold, compared with the mice before the hepatic ischemia surgery, indicating hepatocytic injury caused by the hepatic ischemia surgery. A group treated with 100 mg/kg of a 70% ethanol extract of Moutan Cortex Radicis, compared with the control group, significantly inhibits blood ALT activity, and a group treated with 30 or 300 mg/kg of a 70% ethanol extract of Moutan Cortex Radicis, compared with the control group, tended to slightly inhibit blood ALT activity.

Example 3. Protective Effect of Moutan Cortex Radicis Extract Against Hepatic Ischemia and Reperfusion Injury In this example, to confirm a liver protective effect according to the treatment of a fraction of a Moutan Cortex Radicis extract, blood ALT activity and a hepatic TLR4 or IL-1β protein expression level of a water, butanol, hexane or ethyl acetate (EA) fraction of a 70% ethanol extract of Moutan Cortex Radicis were compared according to the methods described in Examples 1-3, 1-6 and 1-7.

3-1. Blood ALT Activity

Consequently, as shown in FIG. 2, in the groups treated with the water, hexane and butanol fractions of the Moutan Cortex Radicis extract, compared with the control group, there were no significant differences in blood ALT activity. In contrast, in the groups treated with the ethyl acetate fraction of the Moutan Cortex Radicis extract (1.25, 2.5 and 5 mg/kg), compared with the control group, the blood ALT activity was significantly inhibited in all dose groups, and a significantly excellent blood ALT activity inhibitory effect was exhibited even with a smaller amount of administration than the group treated with the 70% ethanol extract of Moutan Cortex Radicis of Example 2 (considering a percent yield of 13.3%).

3-2. TLR4 and IL-1β Protein Expression Levels in Liver

While the TLR4 protein expression level in liver tissue was significantly increased 1.6-fold in the case of ischemia and reperfusion, compared with the control group, as shown in FIG. 3A, it was confirmed that the administration of 1.25 and 2.5 mg/kg of the ethyl acetate fraction of the 70% ethanol extract of Moutan Cortex Radicis and 100 mg/kg of the 70% ethanol extract significantly inhibited the TLR4 protein expression. While the IL-1β protein expression level in liver tissue was significantly increased 1.7-fold in the case of ischemia and reperfusion, compared with the control group, as shown in FIG. 3B, it was confirmed that the administration of 1.25 and 2.5 mg/kg of the ethyl acetate fraction of the 70% ethanol extract of Moutan Cortex Radicis significantly inhibited the IL-1β protein expression, and 100 mg/kg of the 70% ethanol extract thereof tended only to reduce the IL-1β protein expression.

Taken together, compared with the 70% ethanol extract of Moutan Cortex Radicis, the water, butanol, hexane or ethyl acetate (EA) fraction thereof exhibited a more excellent blood ALT activity inhibitory effect and an excellent TLR4 or IL-1β protein expression inhibitory effect in the liver. Particularly, it was confirmed that, among these fractions, the ethyl acetate fraction exhibited the most excellent effect, that is, the most excellent liver protective effect. Therefore, the following example was carried out to conduct a more detailed experiment on the ethyl acetate fraction.

Example 4. Protective Effect of Ethyl Acetate Fraction of Moutan Cortex Radicis Extract Against Acute Hepatic Failure Caused by GalN/LPS In this example, to confirm whether the ethyl acetate fraction of the Moutan Cortex Radicis extract as confirmed from the above examples affected the acute hepatic failure caused by GalN/LPS, an experiment was carried out according to the methods described in Examples 1-3, 1-4, 1-6 and 1-7.

4-1. Blood ALT Activity

As a result, before the treatment of the fraction, the blood ALT activity in the control group was 45.0±8.7 U/L, and 6 hours after the GalN/LPS administration, the blood ALT activity was increased 16.7-fold, compared with the control group. As shown in FIG. 4, it was confirmed that the administration of 1.25, 2.5 and 5 mg/kg of the ethyl acetate fraction of the 70% ethanol extract of Moutan Cortex Radicis significantly inhibited an ALT increase caused by GalN/LPS, and particularly, the administration of 1.25 and 2.5 mg/kg of the fraction thereof exhibited an excellent ALT activity inhibitory effect, compared with the administration of 100 mg/kg of the 70% ethanol extract of Moutan Cortex Radicis (considering a percent yield of 13.3%).

4-2. TLR4 Protein Expression Level in Liver

In addition, when GalN/LPS was treated before the treatment of the fraction, a TLR4 protein expression level in liver tissue was significantly increased 2.1-fold, compared with the control group, but as shown in FIG. 5, when 1.25 and 2.5 mg/kg of the ethyl acetate fraction of the 70% ethanol extract of Moutan Cortex Radicis were administered, it was confirmed that the TLR4 protein expression was significantly inhibited, and the administration of 100 mg/kg of the 70% ethanol extract tended only to reduce the TLR4 protein expression.

Example 5. Protective Effect of Fraction of Moutan Cortex Radicis Extract Against APAP-Induced Liver Injury In this example, to confirm whether the ethyl acetate fraction of the Moutan Cortex Radicis extract as confirmed from the above examples affected APAP-induced liver injury, an experiment was carried out according to the methods described in Examples 1-3, and 1-5 to 1-7.

5-1. Blood ALT Activity

As a result, before the treatment of the fraction, the blood ALT activity in the control group was 35.2±8.0 U/L, and 24 hours after the APAP administration, the blood ALT activity was increased 249.0-fold, compared with the control group. However, as shown in FIG. 6, it was confirmed that the administration of 1.25 mg/kg of the ethyl acetate fraction of the 70% ethanol extract of Moutan Cortex Radicis significantly inhibited an ALT increase caused by APAP, and 2.5 and 5 mg/kg of the ethyl acetate fraction thereof tended only to inhibit the ALT increase caused by APAP. In contrast, it was confirmed that the administration of 100 mg/kg of the 70% ethanol extract of Moutan Cortex Radicis did not affect the ALT increase caused by APAP.

5-2. Lipid Peroxidation in Liver

In addition, before the fraction treatment, a concentration of malondialdehyde (MDA) in the liver, which is the final product of lipid peroxidation, in the control group was 0.26±0.01 nmol/mg protein. Twenty-four hours after the APAP administration, the MDA concentration in the liver was increased 2.4-fold, compared with the control group. However, as shown in FIG. 7, it was confirmed that the administration of 1.25 mg/kg of the ethyl acetate fraction of the 70% ethanol extract of Moutan Cortex Radicis significantly inhibited the MDA increase caused by APAP, but the administration of 100 mg/kg of the 70% ethanol extract of Moutan Cortex Radicis did not affect the MDA increase caused by APAP.

Taken together, compared with the 70% ethanol extract of Moutan Cortex Radicis, it was confirmed that the ethyl acetate fraction exhibited a significantly excellent liver protective effect, and therefore it is expected to be effectively used as a composition for preventing or treating a liver disease.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

A composition according to the present invention includes a fraction of a Mouton Cortex Radicis extract as an active ingredient, and it was specifically confirmed that a blood ALT concentration, which is an indicator of liver injury, can be effectively reduced, an increase in TLR4 or IL-1β protein expression in the liver is inhibited, and lipid peroxidation in the liver can also be inhibited using the composition. Therefore, as the present invention uses a natural substance-derived active ingredient, the composition can exhibit excellent liver protective efficacy, can have almost no toxicity and side effects, and can be used in a body for a long period of time, and thus is expected to be effectively used in prevention or treatment of a liver disease.

The invention claimed is:

1. A method for preventing or treating a liver disease, comprising:
    administering composition comprising an ethyl acetate fraction of a Moutan Cortex Radicis extract as an active ingredient into a subject,
    wherein the extract is obtained through extraction using ethanol.

2. The method of claim 1, wherein the liver disease is selected from the group consisting of hepatitis, hepatotoxicity, cholestasis, fatty liver, liver cirrhosis, liver ischemia, an alcoholic liver disease, a liver abscess, hepatic coma, liver atrophy, and liver cancer.

3. The method of claim 1, wherein the composition inhibits an increase in blood alanine aminotransferase (ALT) concentration.

4. The method of claim 1, wherein the composition inhibits an increase in toll-like receptor (TLR) 4 or interleukin 1 beta (IL-1β) protein expression level in the liver.

5. The method of claim 1, wherein the composition inhibits lipid peroxidation in the liver.

6. A method of improving a liver disease, the method comprising
    administering a health functional food composition comprising an ethyl acetate fraction of a Moutan Cortex Radicis extract as an active ingredient into a subject,
    wherein the extract is obtained through extraction using ethanol.

* * * * *